United States Patent [19]
Ebner et al.

[11] Patent Number: 5,874,646
[45] Date of Patent: Feb. 23, 1999

[54] PREPARATION OF PHENOL OR PHENOL DERIVATIVES

[75] Inventors: Jerry R. Ebner, St. Peters, Mo.; Timothy R. Felthouse, Austin; Denton C. Fentress, Leander, both of Tex.

[73] Assignee: Solutia Inc., St. Louis, Mo.

[21] Appl. No.: 693,432

[22] Filed: Aug. 7, 1996

[51] Int. Cl.$^6$ ............................................. C07C 37/60
[52] U.S. Cl. ............................................ 568/771; 568/800
[58] Field of Search ........................ 502/66, 74; 568/771, 568/800

[56] References Cited

U.S. PATENT DOCUMENTS

| | | | |
|---|---|---|---|
| 4,157,338 | 6/1979 | Haag | 502/74 |
| 4,258,222 | 3/1981 | Möhring et al. | 568/863 |
| 4,344,868 | 8/1982 | Chang | 502/74 |
| 4,396,783 | 8/1983 | Esposito | 568/771 |
| 4,444,909 | 4/1984 | Chang et al. | 518/716 |
| 4,578,521 | 3/1986 | Chang | 568/771 |
| 4,980,326 | 12/1990 | Hinnenkamp | 502/66 |
| 4,982,013 | 1/1991 | Gubelmann et al. | 568/771 |
| 5,001,280 | 3/1991 | Gubelmann et al. | 568/716 |
| 5,019,657 | 5/1991 | Gubelmann et al. | 568/774 |
| 5,055,623 | 10/1991 | Gubelmann et al. | 568/800 |
| 5,110,995 | 5/1992 | Kharitonov et al. | 568/800 |
| 5,171,553 | 12/1992 | Li et al. | 423/239 |
| 5,235,111 | 8/1993 | Clerici | 568/399 |
| 5,502,259 | 3/1996 | Zakoshansky et al. | 568/754 |

FOREIGN PATENT DOCUMENTS

| | | |
|---|---|---|
| 0 038 141 A2 | 10/1981 | European Pat. Off. . |
| 0 186 479 A2 | 7/1986 | European Pat. Off. . |
| 0 211 228 A1 | 2/1987 | European Pat. Off. . |
| 0 306 170 A1 | 3/1989 | European Pat. Off. . |
| 0 406 050 A2 | 6/1990 | European Pat. Off. . |
| Hei 5-16179 | 2/1993 | Japan . |
| 2 010 790 | 4/1994 | Russian Federation . |
| 2 116 974 | 3/1993 | United Kingdom . |
| WO 95/012222 | 1/1995 | WIPO . |
| WO 95/27560 | 10/1995 | WIPO . |
| WO 95/27691 | 10/1995 | WIPO . |

OTHER PUBLICATIONS

Dvorak et al. (1970) *Determination Of The Specific Copper Surface Area By Chromatographic Technique;* Journal of Catalysis 18, 108–114, Academic Press, Inc.

Evans et al. (1983) *On The Determination Of Copper Surface Area By Reaction With Nitrous Oxide;* Applied Catalysis 7, 75–83, Elsevier Science Publishers B.V.

Iwamoto et al. (1983) *Catalytic Oxidation By Oxide Radical Ions. 1. One–Step Hydroxylation Of Benzene To Phenol Over Group 5 And 6 Oxides Supported On Silica Gel;* The Journal of Physical Chemistry 87, No. 6, The American Chemical Society.

Ono et al. (1988) *Functionalization Of Benzene By Its Reaction With Nitrogen Oxides Over Solid–Acid Catalysts,* Heterogeneous Catalysis and Fine Chemicals pp. 75–82, Elsevier Science Publishers B.V., Amsterdam.

Suzuki et al. (1988) *Hydroxylation Of Benzene With Dinitrogen Monoxide Over H–ZSM–5 Zeolite,* Chemistry Letters pp. 953–956, The Chemical Society of Japan.

Panov et al. (1990) *The Role Of Iron In $N_2O$ Decomposition On ZSM–5 Zeolite And Reactivity Of The Surface Oxygen Formed,* Journal of Molecular Catalysis 61, 85–97, Elsevier Sequoia.

Sobolev et al. (1991) *Anomalously Low Bond Energy Of Surface Oxygen On FeZSM–5 Zeolite,* Mendeleev Communications, No. 1, pp. 29–30.

Zholobenko (1993) *Preparation Of Phenol Over Dehydroxylated HZSM–5 Zeolites,* Mendeleev Communications, pp. 23–24.

Hafele et al. (1996) *Hydroxylation of Benzene on ZSM5 Type Catalysts,* DGMK–Conference, Catalysis On Solid Acids And Bases pp. 243–251.

Vereshchagin et al, *Conversion Of Ethane On Zeolite Catalysts In The Presence Of Oxygen And Nitrogen* (I) *Ox De, Izv. Akad. Naur SSSR,* (1988), 1718–1722.

Li et al. (1992) *Catalytic Decomposition of Nitrous Oxide on Metal Exchanged Zeolites;* Applied Catalysis B: Environmental 1, L21–29; Elsevier Science Publishers B.V., Amsterdam.

Sobolev et al. (1993) *Catalytic Properties of ZSM–5 Zeolites in $N_2O$ Decomposition: The Role of Iron;* Journal of Catalysis 139, 435–443; Academic Press, Inc.

Sobolev et al. (1993) *Stoichiometric Reaction of Benzene with α–Form of Oxygen on FeZSM–5 Zeolites. Mechanism of Aromatics Hydroxlation by $N_2O$;* Journal of Molecular Catalysis 84, 117–124; Elsevier Science Publishers B.V., Amsterdam.

Panov et al. (1992) *Oxidation of Benzene to Phenol by Nitrous Oxide Over Fe–ZSM–5 Zeolites;* Applied Catalysis A: General 82, 31–36; Elsevier Science Publishers B.V., Amsterdam.

Kharitonov et al. (1993) *Ferrisilicate Analogs of ZSM–5 Zeolite as Catalysts for One Step Oxidation of Benzene to Phenol;* Applied Catalysis A: General 98, 33–43, Elsevier Science Publishers B.V., Amsterdam.

Burch et al. (1993) *Factors Affecting the Deactivation of Various Zeolites Used as Catalysts for the Direct Partial Oxidation of Benzene to Phenol;* Applied Catalysis A: General 106, 167–183, Elsevier Science Publishers B.V., Amsterdam.

Burch et al. (1993) *Investigation of Zeolite Catalysts for the Direct Partial Oxidation of Benzene to Phenol;* Applied Catalysis A: General 103, 135–162, Elsevier Science Publishers B.V., Amsterdam.

(List continued on next page.)

*Primary Examiner*—Michael Lewis
*Assistant Examiner*—Peter DiMauro
*Attorney, Agent, or Firm*—Arnold White & Durkee

[57] ABSTRACT

In a process for converting an aromatic compound such as benzene into its hydroxylated derivative, generation of carbon monoxide during catalyst regeneration is reduced if the catalyst is a zeolite that contains ruthenium, rhodium, platinum, palladium, or irridium.

8 Claims, 2 Drawing Sheets

OTHER PUBLICATIONS

Burch et al. (1993) *Direct Partial Oxidation of Benzene to Phenol on Zeolite Catalysts;* Applied Catalysis A: General 86, 139–146, Elsevier Science Publishers B.V., Amsterdam.

Panov et al. (1993) *Oxidative Hydroxylation Using Dinitrogen Monoxide; A Possible Route for Organic Synthesis Over Zeolites,* Applied Catalysis A: General, 98, 1–20, Elsevier Science Publishers B.V., Amsterdam.

Derwent abstract; JP 5 009 142 (1994).

Derwent abstract, JP 4 334 333 (1993).

Derwent abstract, JP 4 021 645 (1993).

Derwent abstract, JP 6 009 464 (1995).

Derwent abstract, JP 6 040 976 (1995).

Derwent abstract, EP 406 050 (Jun. 15, 1990).

Patent Abstracts of Japan, vol. 015, No. 377 (Sep. 24, 1991).

PREPARATION OF PHENOL OR PHENOL DERIVATIVES

BACKGROUND OF THE INVENTION

The present invention relates to a process for converting benzene or derivatives thereof to phenol or related compounds, and also relates to improved catalysts for use in that process.

Phenol or a derivative thereof can be produced by a single-step oxidative hydroxylation of benzene or a derivative thereof, using nitrous oxide over a catalyst. For example, PCT publication WO 9527560 describes such a process that employs a zeolite catalyst whose performance is enhanced by hydrothermal treatment.

The catalyst that is used in such a process has to be regenerated periodically. One problem with the regeneration step is that it generates carbon monoxide. Because emissions of carbon monoxide into the atmosphere are limited by environmental regulations in the United States and other countries, when this compound is produced during catalyst regeneration it must be recovered and/or converted to another compound. These additional steps make the overall process more expensive.

A need exists for improved catalysts for conversion of an aromatic hydrocarbon such as benzene to phenol or another desired product. In particular, a need exists for catalysts that can be used in such processes with good activity, stability, and selectivity, and that would also reduce the amount of carbon monoxide created during catalyst regeneration.

SUMMARY OF THE INVENTION

In the present invention, phenols or substituted phenols can be prepared using a process in which an aromatic substrate is hydroxylated in a direct fashion using a zeolite that contains ruthenium, rhodium, platinum, palladium, or iridium.

One aspect of the present invention concerns a process for catalytic hydroxylation of an aromatic compound. The process comprises contacting an aromatic compound such as benzene with a zeolite catalyst that comprises at least one metal selected from the group consisting of ruthenium, rhodium, palladium, platinum, and iridium. The metal is preferably present in a concentration of approximately 0.01–5 weight %, most preferably in a concentration of approximately 0.1–1.5 weight %. The process can further comprise the step of regenerating the catalyst by contacting it with a gas stream that comprises oxygen. As mentioned above, in this regeneration step the amount of CO generated will be substantially less than in prior art processes, because of the catalyst composition.

In one embodiment of the innovation, the zeolite catalyst has the MFI structural type. In a particular embodiment, the catalyst is a ZSM-5 zeolite.

In addition to minimizing CO generation during catalyst regeneration, the catalysts of the present invention are capable of providing high reaction selectivities to phenol, with good conversion, and can be fully regenerated in times less than 12 hours.

DESCRIPTION OF ILLUSTRATIVE EMBODIMENTS

Figure 1:
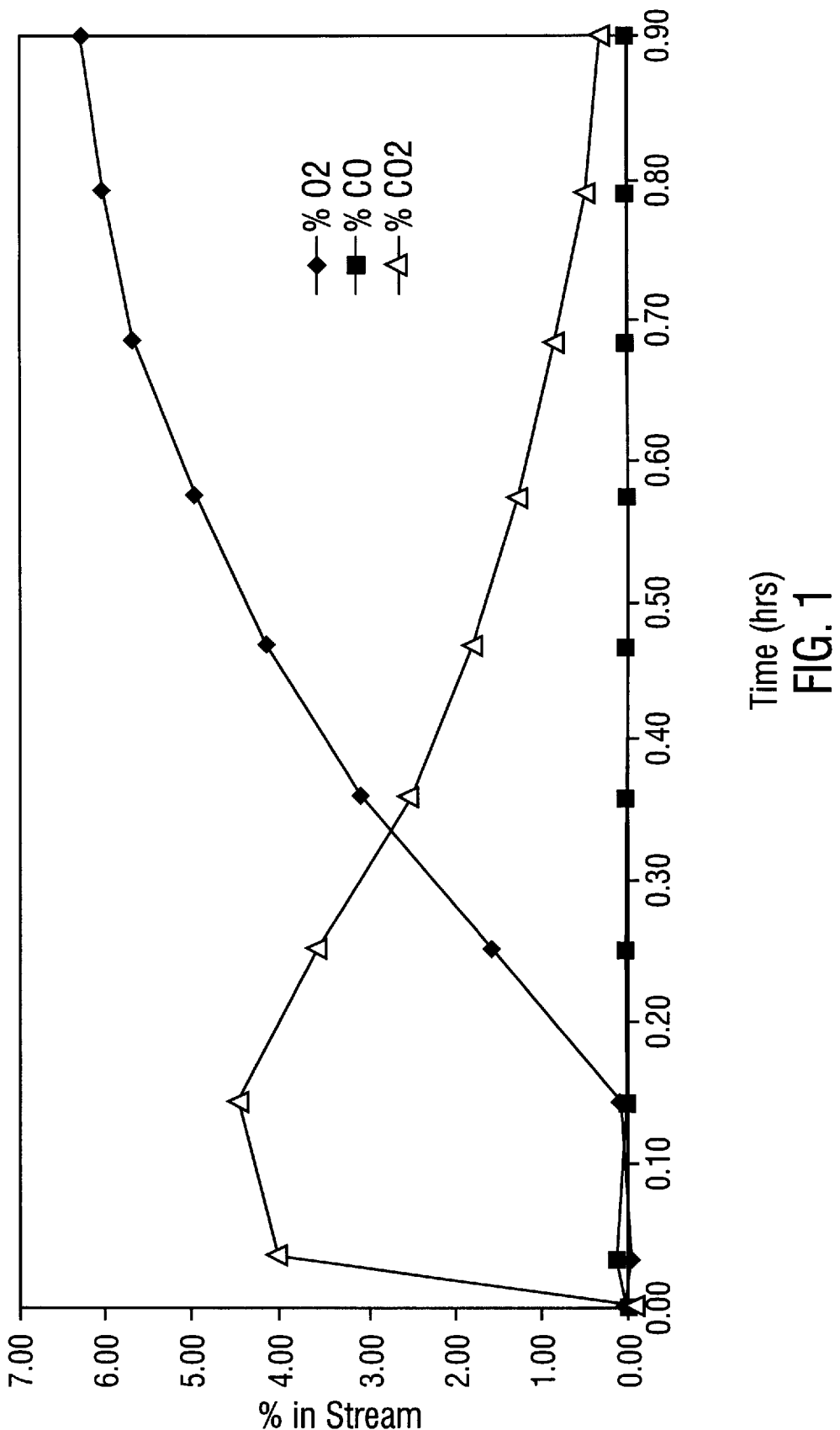
FIG. 1 is a graph of the change over time of the concentration of oxygen, carbon monoxide, and carbon dioxide in regeneration offgas for a catalyst containing Ru.

Aromatic compounds can be hydroxylated using the catalyst of the present invention. Preferred aromatic compounds have from about 6–20 carbon atoms. The compounds can be substituted with one or more substituents such as halogens, aliphatic hydrocarbons having from 1–20 carbon atoms, hydroxyl, carboxyl, amino, nitro, or thio groups, provided however that at least one carbon on the aromatic ring must have a carbon-hydrogen bond. The improved catalysts of the present invention are especially useful in the hydroxylation of benzene and benzene derivatives such as chlorobenzene, fluorobenzene, toluene, ethylbenzene, and the like, into phenol or the corresponding substituted phenol. If phenol itself is the benzene derivative used as the reactant, the reaction products can include polyols such as hydroquinone, resorcinol, and catechol.

The catalysts used in the present invention are modified zeolites. Zeolites having the MFI structural type are preferred, and ZSM-5 catalysts are especially preferred. Such zeolites are commercially available from vendors such as Zeolyst International, UOP, Mobil, and others. The catalyst comprises at least one metal selected from the group consisting of ruthenium, rhodium platinum, palladium, and iridium, preferably in a concentration between about 0.01–5 weight %, most preferably in a concentration between about 0.1–1.5 weight %. The metal can be incorporated into the catalyst by any means known to those skilled in the art for incorporating metals into zeolites. For example, the metal can be added to the zeolite by ion exchange. Alternatively, the metal can be incorporated during synthesis of the catalyst. It is important that the catalyst also contain some amount of iron, preferably in a concentration up to about 5 weight %.

The zeolite catalyst of the present invention can be mixed with silica sols and then extruded into a shape such as a pellet, or spray dried into spherical particles. These forms of the catalyst can be used in various bed configurations, such as fixed bed, fluid bed, or transport bed operations.

The catalyst can optionally be hydrothermally treated. This treatment can be performed by contacting the catalyst with a gas that contains water vapor, in an amount ranging from 1–100 mole % of the gas, at an elevated temperature in the range of approximately 350°–950° C. The gas can of course include gases other than the water vapor. For example, it can include an inert gas such as nitrogen. The duration of the hydrothermal treatment of the catalyst preferably ranges from approximately 0.25 hours to approximately 8 hours. Additional details regarding hydrothermal treatment are given in PCT application WO 9527560, which is incorporated here by reference.

After the catalyst has been prepared, the oxidative hydroxylation reaction is preferably performed by passing a feed gas mixture of an aromatic compound such as benzene, a free oxidant activator such as nitrous oxide, and optionally a diluent gas such as helium, nitrogen, argon, carbon dioxide or the like, to a bed of the catalyst at a temperature in the range of approximately 250°–650° C. The contact time (defined as cc catalyst/cc total flow/sec) in the catalyst bed is preferably between 0.25–4 sec. The feed composition and process conditions can be varied by those skilled in the art to maximize the desired product.

Regeneration of the catalyst is preferably done by passing a gas stream comprising oxygen, and optionally comprising an inert diluent, over the catalyst. The regeneration is preferably done at a temperature between about 350°–800° C., for a time ranging from about 0.25 hr to about 12 hr.

The present invention can be further understood from the following examples.

EXAMPLE 1

To a 4 liter beaker fitted with a mechanical stirrer was added 2240 g of water and 5.37 g of $RuCl_3 \cdot 1.84\ H_2O$ (Johnson Matthey, Aesar, with water content based on 42.01% Ru assay). The pH of this solution was 1.9. To this stirred solution was added 500.0 g of PQ Valfor® CBV 3020 H-ZSM-5 powder having an $SiO_2/Al_2O_3$ ratio of 30 (% $Na_2O=0.02$). The brown slurry converted to a gray color over a 24 hr. period at room temperature. The slurry was collected on a 2-liter medium porosity filter with a slight reddish brown tint to the filtrate (maximum % Ru=0.45). The wet cake was resuspended in 2.5 liters of water, stirred for about 18 hr., then collected on the filter again. After a second resuspension of the wet cake in 2.5 liters of water, the filtrate showed only a trace of $Cl^-$ ($Ag^+$ test). The wet cake was broken to below an 18 mesh screen and dried in a vacuum oven at 100° C. for at least 18 hr. A total of 473.3 g of gray powder was recovered from the vacuum oven.

A portion of the gray powder was calcined for 6 hr at 500° C. in air. The calcined powder was placed in a vacuum desiccator which was humidified with water. A total of 2.91 g (9.7%) water was taken up by 30.03 g of calcined powder. To this hydrated powder was added 1.0 g of stearic acid (Emersol 132, average particle size of 70 $\mu$m). The mixture was further blended with 18.75 g of Nalco 2327 colloidal silica (40% $SiO_2$, $NH_4^+$ stabilized). Another 0.88 g of hydrated Ru, H-ZSM-5 powder was added and mixed to give a charcoal black mass. The mass was very cohesive and was fed to a Bonnot lab extruder with 1/16" holes on the extrusion plate. The 1/16" extrudates were vacuum dried at 100° C. and calcined at 500° C. in air for 6 hr. The calcined extrudates had an average axial crush strength of 5.1 lbs for 1/8" long pieces.

The catalyst as prepared above (7.602 g in the form of calcined extrudates) was charged into a stainless steel reactor with a feed of 240 cc/min He, 65 cc/min $N_2O$, and 16.35 cc/min benzene. The process was run for 15 hours. Afterwards, the catalyst was regenerated using a 500° C. bath, 160 cc/min He, and 40 cc/min $O_2$.

The average reaction conversion was 0.33 mmol of benzene per gram of catalyst per hour, with 98% selectivity to phenol.

EXAMPLE 2

2.13 g of $(NH_3)_6RuCl_3$ was dissolved in 200 ml of deionized water in a one liter beaker. To this was added 70 g of H-ZSM5 zeolite (PQ CBV5020). The mixture was stirred overnight, and the slurry was filtered, washed with 3×250 ml of deionized water, and the solid dried at 120° C. under nitrogen. The solid was then calcined at 600° C. for 90 min. This is an ion exchange method of Ru addition.

Figure 2:
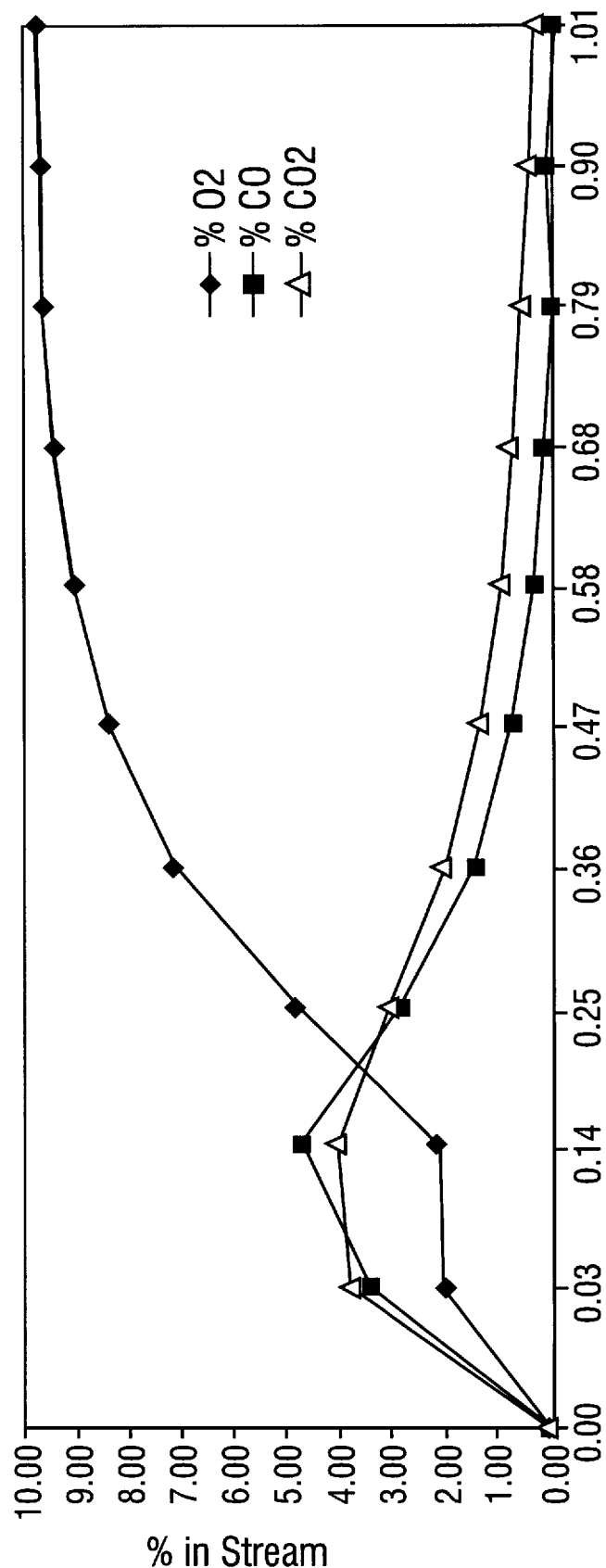
FIG. 2 is a similar graph for a catalyst that did not contain added metal.

This Ru-containing catalyst and the CBV5020 catalyst that did not contain Ru were each run in the nitrous oxide reaction of benzene to phenol. Then both catalysts were regenerated in an oxygen stream at 525° C. furnace temperature. FIGS. 1 and 2 show the concentration of $O_2$, CO, and $CO_2$ in the regeneration offgas for the Ru containing catalyst and the catalyst that did not contain Ru, respectively. The CO concentration in FIG. 1 is substantially lower than in FIG. 2.

The preceding description of specific embodiments of the present invention is not intended to be a complete list of every possible embodiment of the invention. Persons skilled in this field will recognize that modifications can be made to the specific embodiments described here that would be within the scope of the present invention.

We claim:

1. A process for catalytic hydroxylation of an aromatic compound, comprising contacting an aromatic compound with nitrous oxide and a zeolite catalyst that comprises at least one metal selected from the group consisting of ruthenium, rhodium, platinum, palladium, and iridium, the metal being present in the zeolite catalyst in a concentration between approximately 0.01–5 weight percent.

2. The process of claim 1, where the metal is present in the catalyst in a concentration between approximately 0.1–1.5 weight percent.

3. The process of claim 1, where the zeolite catalyst has the MFI structural type.

4. The process of claim 1, where the zeolite catalyst is a ZSM-5 catalyst.

5. The process of claim 1, where the aromatic compound is benzene.

6. The process of claim 1, further comprising the step of regenerating the catalyst by contacting it with a gas stream that comprises oxygen.

7. The process of claim 6, where the gas stream further comprises an inert gas.

8. A process for catalytic hydroxylation of benzene, comprising (a) contacting benzene with nitrous oxide and a ZSM-5 zeolite catalyst that comprises at least one metal selected from the group consisting of ruthenium and rhodium, the metal being present in the zeolite catalyst in a concentration between approximately 0.1–1.5 weight percent, and (b) regenerating the catalyst by contacting it with a gas stream that comprises oxygen.

* * * * *